United States Patent [19]

Rosenbluth

[11] Patent Number: 4,893,623

[45] Date of Patent: * Jan. 16, 1990

[54] METHOD AND APPARATUS FOR TREATING HYPERTROPHY OF THE PROSTATE GLAND

[75] Inventor: Robert F. Rosenbluth, Laguna Niguel, Calif.

[73] Assignee: Advanced Surgical Intervention, Inc., San Clemente, Calif.

[*] Notice: The portion of the term of this patent subsequent to Aug. 9, 2005 has been disclaimed.

[21] Appl. No.: 120,981

[22] Filed: Nov. 20, 1987

Related U.S. Application Data

[63] Continuation-in-part of Ser. No. 939,754, Dec. 9, 1986, Pat. No. 4,762,128.

[51] Int. Cl.$^4$ .............................................. A61M 29/00
[52] U.S. Cl. ...................................... 606/192; 604/104
[58] Field of Search ............................... 128/343, 344; 604/96–104

[56] References Cited

U.S. PATENT DOCUMENTS 3,509,883  5/1970  Dibelius ........................... 128/348
3,657,744  4/1972  Ersek .................................... 3/1

(List continued on next page.)

FOREIGN PATENT DOCUMENTS 0183372  6/1986  European Pat. Off. .
0221570  5/1987  European Pat. Off. .
1205743  9/1970  United Kingdom .

OTHER PUBLICATIONS

Burhenne, et al., "Prostatic Hyperplasia: Radiological Intervention".
Cragg, et al., "Nonsurgical Placement of Arterial Endoprostheses: A New Technique Using Nitinol Wire".
Dotter, "Transluminally-Placed Coilspring Endarterial Tube Grafts".
Dotter, et al., "Transluminal Expandable Nitinol Coil Stent Grafting: Preliminary Report".
Maas, et al., "Radiological Follow-up of Translumi-nally Inserted Vascular Endoprostheses: An Experimental Study Using Expanding Spirals".
Palmaz, et al., "Expandable Intraluminal Graft: A Preliminary Study", Radiology, Program Abstracts (Oct. 16-18, 1984).
Palmaz, et al., "Atherosclerotic Rabbit Aortas: Expandable Intraluminal Grafting", Radiology, 160:723 (Sep. 1986).
Palmaz, et al., "Expandable Intraluminal Grafting in Atherosclerotic Rabbit Aortas", Radiology, Program Abstracts (Oct. 1985).
Ring, et al., "A Simple, Indwelling, Biliary Endoprosthesis Made from Commonly Available Catheter Material".
Wright, et al., "Percutaneous Endovascular Stents: An Experimental Evaluation".
Additionally enclosed are copies of Chapters 1, 6 and 8 from "Benign Prostatic Hypertrophy", edited by Frank Hinman, M.D., which provide general background material.

Primary Examiner—Dalton L. Truluck
Attorney, Agent, or Firm—Knobbe, Martens, Olson & Bear

[57] ABSTRACT

Disclosed is a method and apparatus for treatment of hypertrophy of the prostate gland. The apparatus comprises an expansion catheter having an expandable tubular stent associated therewith, adapted for transurethral insertion via the external opening of the urethra and placement within a stenotic region of the urethral lumen caused by a hypertrophied prostate gland. Force exerted by the expansion catheter upon the tubular expandable stent causes an opening of the lumen within the prostatic urethra. Removal of the expansion catheter, leaving in place the expanded tubular stent, ensures a long-term patency of the urethral lumen. Also disclosed is an apparatus for reducing in diameter and thereafter removing a previously implanted and expanded tubular stent made and inserted in accordance with the present invention.

17 Claims, 5 Drawing Sheets

U.S. PATENT DOCUMENTS

| | | | |
|---|---|---|---|
| 3,713,175 | 1/1973 | Weisman | 3/1 |
| 3,868,956 | 3/1975 | Alfidi et al. | 128/345 |
| 3,977,408 | 8/1976 | MacKew | 128/349 |
| 3,993,078 | 11/1976 | Bergentz et al. | 128/334 |
| 3,996,938 | 12/1976 | Clark, III | 128/348 |
| 4,130,904 | 12/1978 | Whalen | 3/1.4 |
| 4,140,126 | 2/1979 | Choudhury | 128/325 |
| 4,143,651 | 3/1979 | Patel | 604/100 |
| 4,183,102 | 1/1980 | Guiset | 3/1.4 |
| 4,292,974 | 10/1981 | Fogarty et al. | 128/344 |
| 4,299,226 | 11/1981 | Banka | 128/344 |
| 4,300,244 | 11/1981 | Bokros | 3/1.4 |
| 4,327,709 | 5/1982 | Hanson et al. | 128/1 D |
| 4,434,797 | 3/1984 | Silander | 128/343 |
| 4,444,188 | 4/1984 | Bazell et al. | 128/348 |
| 4,483,340 | 11/1984 | Fogarty et al. | 128/344 |
| 4,493,711 | 1/1985 | Chin et al. | 604/271 |
| 4,503,569 | 3/1985 | Dotter | 3/1.4 |
| 4,512,338 | 4/1985 | Balko et al. | 128/1 R |
| 4,553,545 | 11/1985 | Maas | 128/341 |
| 4,560,374 | 12/1985 | Hammerslag | 128/344 X |
| 4,580,568 | 4/1986 | Gianturco | 128/345 |
| 4,641,653 | 2/1987 | Rockey | 128/344 |
| 4,649,922 | 3/1987 | Wiktor | 128/344 |
| 4,655,771 | 4/1987 | Wallsten | 623/1 |
| 4,660,560 | 4/1987 | Klein | 128/344 |
| 4,702,252 | 10/1987 | Brooks et al. | 128/344 |
| 4,733,665 | 3/1988 | Palmaz | 128/343 |
| 4,739,762 | 4/1988 | Palmaz | 128/343 |
| 4,740,207 | 4/1988 | Kreamer | 623/1 |

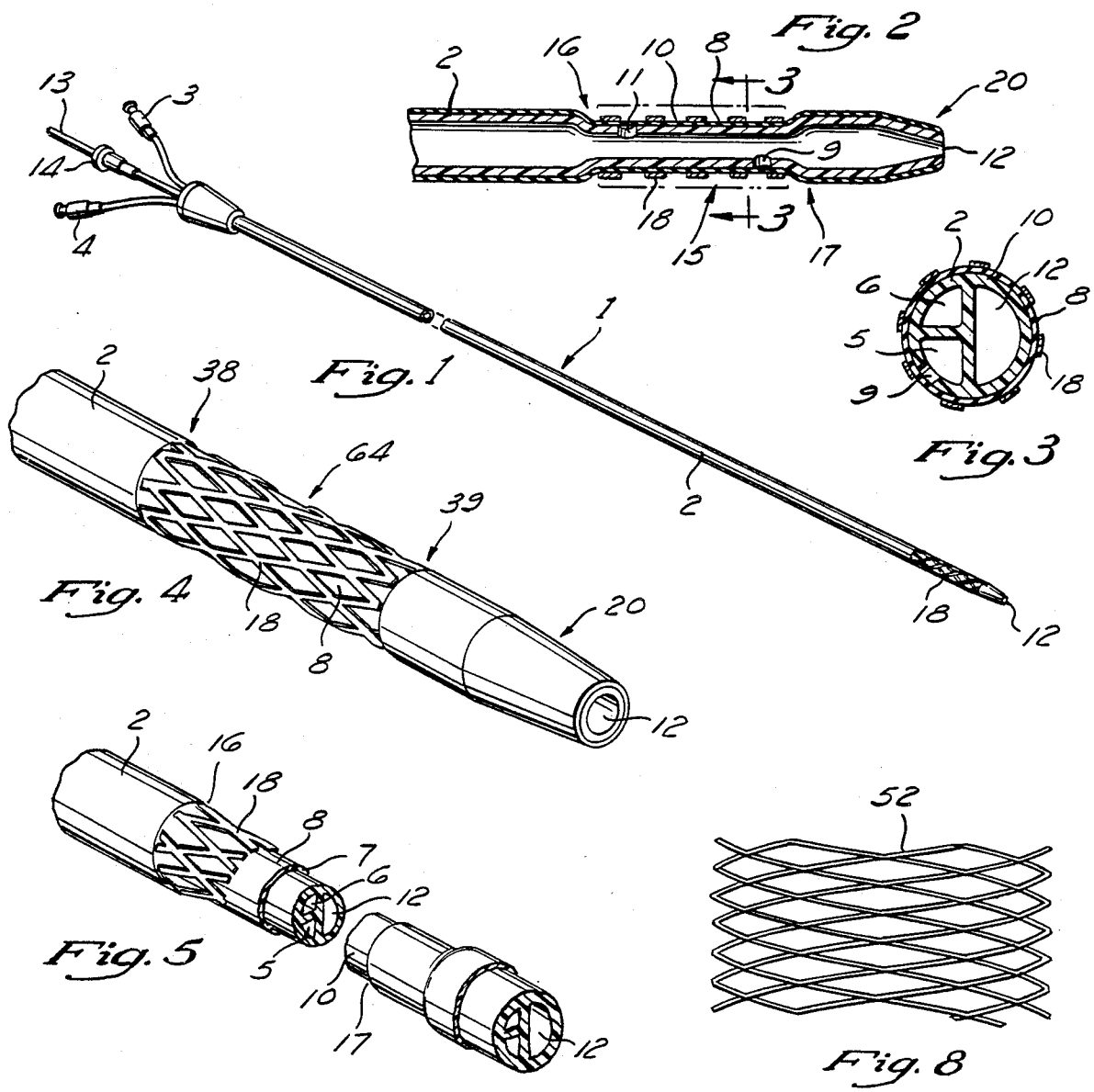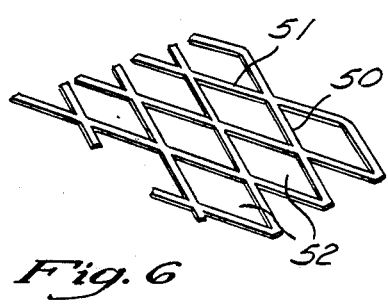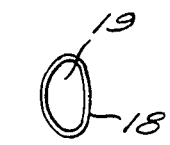

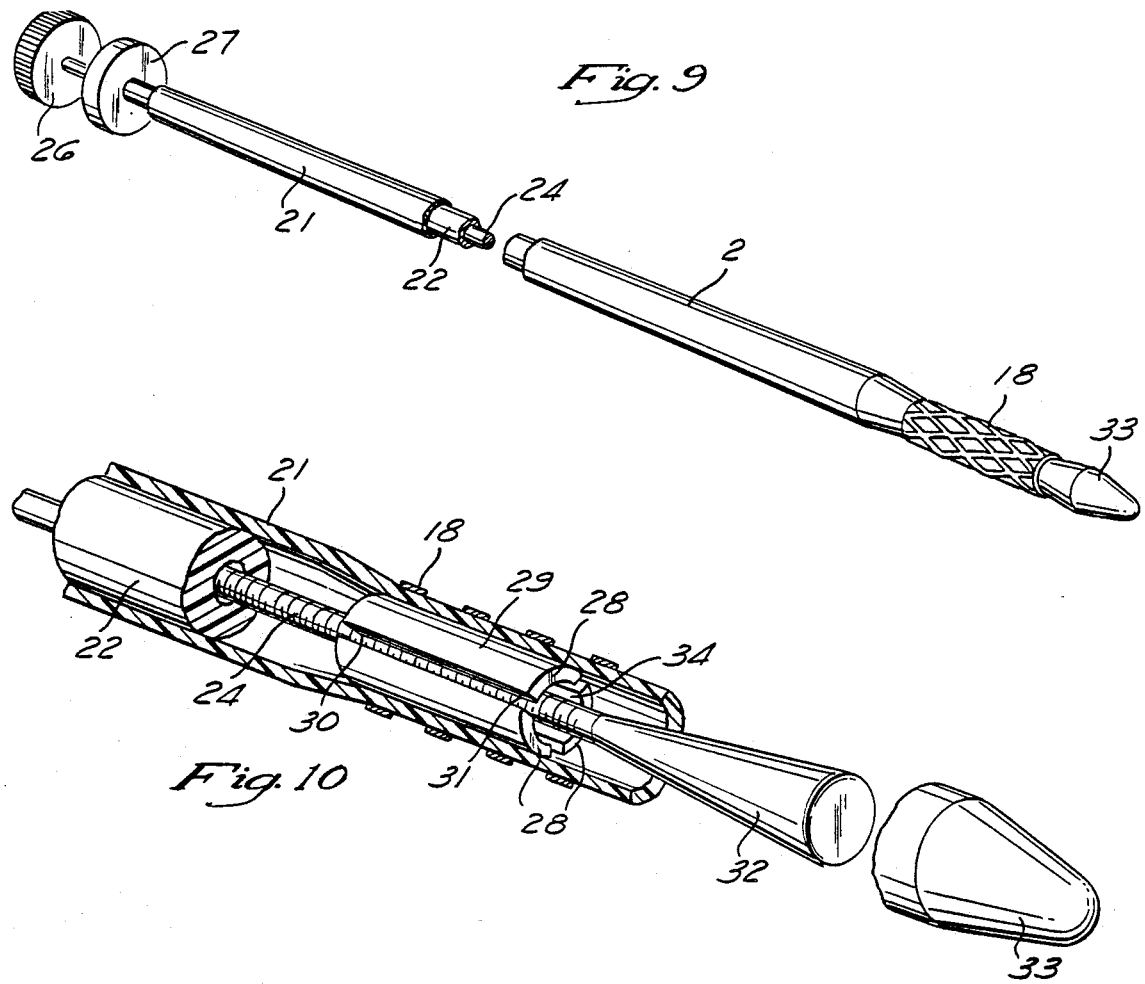
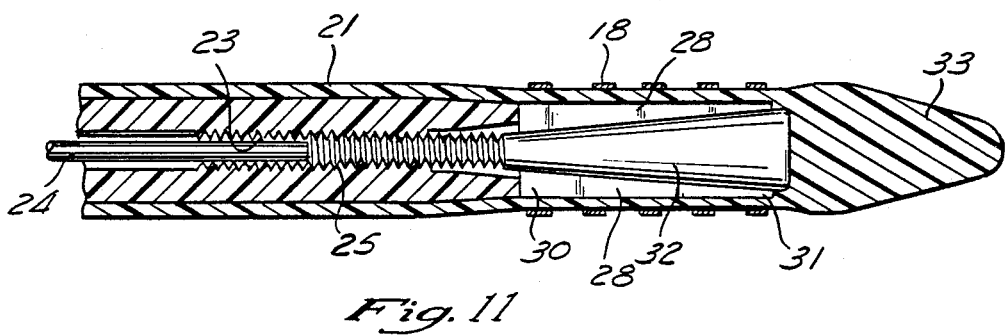

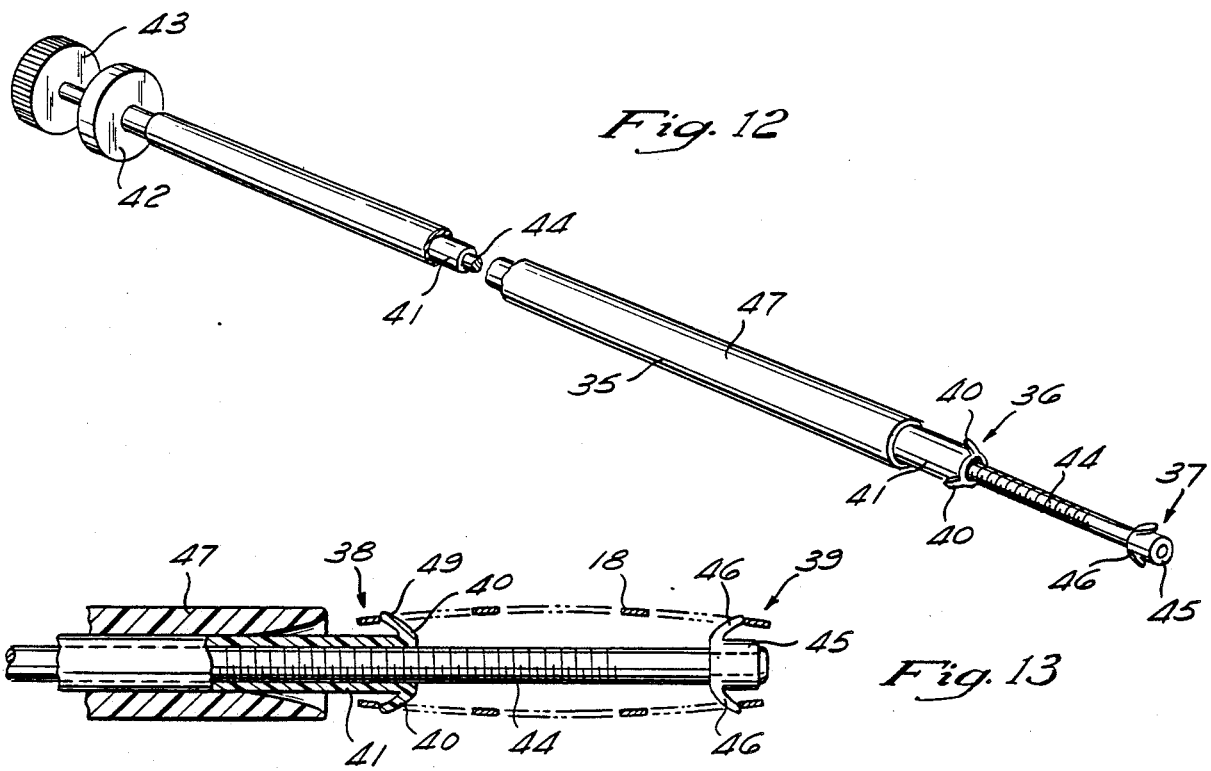
Fig. 12
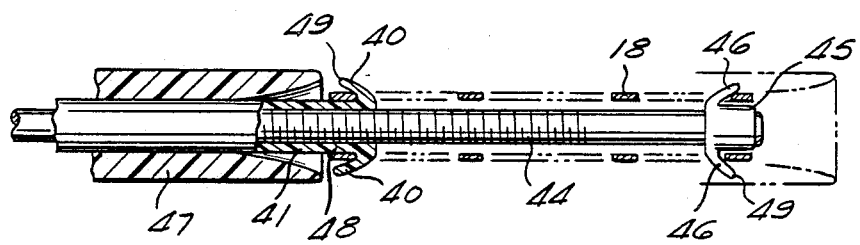
Fig. 13
Fig. 14
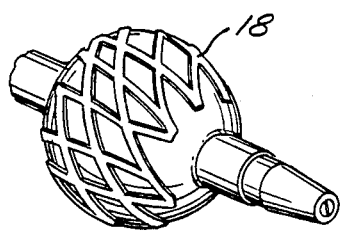
Fig. 15

METHOD AND APPARATUS FOR TREATING HYPERTROPHY OF THE PROSTATE GLAND

CROSS-REFERENCE TO RELATED APPLICATION

This application is a continuation of application Ser. No. 939,754 filed Dec. 9, 1986 now U.S. Pat. No. 4,762,128.

BACKGROUND OF THE INVENTION

The surgical treatment of hypertrophy of the prostate gland has been a routine procedure in the operating room for many years. One method of surgical treatment is open prostectomy whereby an incision is made to expose the enlarged prostate gland and the hypertrophied tissue is removed under direct vision. Another method, which has gained increasing usage in recent years, is transurethral resection. In this procedure, an instrument called a resectoscope is placed into the external opening of the urethra and an electrosurgical loop is used to carve away sections of the prostate gland from within the prostatic urethra under endoscopic vision. For an interesting historical survey of prostate surgery see the book "Benign Prostatic Hypertrophy" edited by Frank Hinman, M.D. and particularly the chapter entitled "Prostectomy, Past and Present" by Geoffrey D. Chisholm, M.D.

The technique of transurethral resection offers many benefits to the patient as compared to open prostectomy. Using this technique the trained urologist can remove the hypertrophied prostate with less discomfort, a shorter hospital stay, and lower rates of mortality and morbidity. Over 333,000 patients underwent this procedure in the United States in 1985, with an average length of stay in the hospital of six days.

Notwithstanding the significant improvement in patient care resulting from the widespread application of transurethral resection, there remains a need for a less invasive method of treating the symptoms of prostate disease. Various complications including impotence, incontinence, bleeding, infection, residual urethral obstruction, urethral stricture, and retrograde ejaculation may affect the patient following transurethral resection. A less invasive procedure which would reduce or eliminate the occurrence of these complications and reduce the hospital stay and resulting costs would be of significant value.

One of the earliest applied methods of relieving the acute urinary retention symptomatic of prostate disease was the placement of a catheter through the external urethra opening into the bladder thereby allowing the outflow of urine from the bladder by way of the catheter lumen. These urinary catheters typically employ a balloon at the tip which, when inflated, prevent the expulsion of the catheter from the body. Although this method is effective in achieving urinary outflow, it is generally unacceptable as a long term treatment due to problems of infection, interference with sexual activity, and maintenance and change of catheters.

The use of dilating bougies and sounds for mechanical dilation of the prostatic urethra has been attempted without success in the treatment of prostatic hypertrophy. The fibrous tissue of the prostate gland rebounds after dilation, resulting in only a temporary reduction of urethral constriction. A method of treating prostate disease involving the application of balloon dilatation in a similar manner as in percutaneous transluminal angioplasty of arterial occlusions has been proposed in an article in the September 1984 issue of Radiology, page 655 entitled "Prostatic Hyperplasia: Radiological Intervention" by H. Joachim Burhenne, M.D., et al. This method of prostate dilatation can be expected to have only a short term alleviation of urinary retention as the fibrous and resilient hypertrophied prostate gland will in a relatively short period of time cause the constriction of the prostatic urethra to recur. Also in the angioplasty arts, Palmaz, et al. have described the percutaneous, sheathed insertion of an expandable endoprosthesis into various major arteries of dogs in the article "Expandable Intraluminal Graft: A Preliminary Study" in the July 1985 issue of *Radiology* at page 73.

In contrast to the failure of dilation means to achieve lasting relief of the symptoms of prostatic hyperplasia, the use of bougie, sound and balloon dilation has achieved moderate success in the treatment of ureteral strictures and non-prostatic urethral strictures. See, for example, the abstract entitled "Self Intermittent Dilation Program via Coaxial Balloon Urethral Dilator" by J.D. Giesy, et al. published in the April 1985 issue of the *Journal of Urology*. The contrasting lack of success achieved by dilation in the prostatic urethra is believed to be a function of the differing etiology of the disease. Strictures in the urethra outside of the prostate region are generally due to pathology of the wall and lining of the urethra. Dilation of the urethral wall, in these strictures, causes an enlargement of the urethral lumen through deformation of the urethral wall and lining. In contrast, urethral stenosis resulting from prostatic hypertrophy, is a disease of the enlarged, fibrous, and resilient tissue of the prostate gland. Deformation of the urethral wall will have no lasting effect on relieving the stenosis as the cause of the stenosis is pressure exerted by the hypertrophied prostate gland which, due to its resilient fibrous structure and large bulk, will tend to rebound after temporary compression.

It is important that a method for prostate dilatation, in order to be effective, incorporate means of maintaining the patency of the urethral lumen. Without such means, the patient would be subject to periodically repeated procedures in order to maintain urinary flow.

SUMMARY OF THE INVENTION

The present invention provides a catheter and a stent for relieving the urinary retention symptomatic of hypertrophy of the prostate gland, and which, in use, require little or no hospitalization, and which are unattended by the adverse side effects associated with transurethral resection and other surgical techniques. In addition, the present invention provides a method for making the catheter of the present invention.

Accordingly, there is provided an apparatus for relieving the symptoms of hypertrophy of the prostate gland, comprising an axially elongate catheter shaft comprising at least one lumen therethrough and having an annular recess thereon for receiving a stent; an expandable balloon mounted on the shaft in the recess and in communication with the lumen; and a removably mounted, radially outwardly deformable and expandable tubular stent coaxially disposed about the balloon and situated in the recess, wherein the stent has an opening at each axial end and a central lumen therethrough, wherein the stent is radially expandable by deformation to a preselected configuration in response to pressure from the balloon, and the outside diameter of the stent, in its unexpanded state, is not substantially greater than the outside diameter of the adjacent catheter shaft.

In accordance with another aspect of the present invention, there is provided an apparatus for relieving symptoms of hypertrophy of the prostate gland, comprising an axially elongate catheter shaft having at least one lumen therethrough and having a circumferential recess near one end thereof; an expandable balloon mounted on the shaft in the recess and in communication with the lumen; a removably-mounted, radially outwardly expandable tubular stent coaxially disposed about the balloon, the stent having an opening at each end and a central lumen therethrough; wherein the stent is radially expandable by deformation thereof to a preselected configuration in response to pressure from the balloon, and wherein the outside diameter of the stent, in its unexpanded state, is not substantially greater than the outside diameter of the adjacent catheter.

In one preferred embodiment of the invention, the balloon in its expanded state has a non-cylindrical configuration. In another embodiment, the balloon in its expanded state has a non-circular cross section along its axial length, such as a smaller cross-sectional area at its axial ends than in the central region thereof. In addition, the expanded cross-sectional area of the stent is preferably sufficient to withstand the radial inward pressure of a hypertrophied prostate, and the stent in its expanded state has a fixed geometry, despite such pressure.

In another preferred embodiment, the catheter further comprises a lumen for receiving a steerable guidewire therethrough. The catheter may also include at least one radiopaque marker associated with the axial position of the balloon, and may have a balloon that expands to a configuration having a non-circular cross section, and a convex profile along its axial length.

In yet another preferred embodiment, there is a biocompatible, essentially smooth coating on the stent, such as silicone rubber.

Preferably, the distal end of the catheter comprises a flexible, resilient material in a shape to facilitate insertion into and negotiation of a collapsed lumen with minimal trauma to the lining thereof. More preferably, the distal end of the catheter distal of and adjacent to the annular depression comprises an interior shaft of about the same diameter as the catheter diameter in the annular depression, and an annular piece on top of the inner shaft, adjacent to said stent, and defining the distal end of said recess. The end piece has an outer diameter as great as the outer diameter of the stent and is made of such flexible, resilient material, to retain the stent about the expandable portion of the catheter. The end piece may be mounted onto the interior shaft after the distal end of the expandable region is bonded to the inner shaft. This permits the manufacturer to test the expandable region without using a stent thereabout, and then place the stent thereabout, securing it in the depression by attaching the end piece.

In accordance with another aspect of the present invention, where the catheter has a recess in which a balloon is situated, with an annular stent over the balloon, the portion of the catheter distal of the recess comprises an interior shaft having a diameter no greater than the interior diameter of the stent, wherein the distal end of the balloon is bonded to the interior shaft; and an exterior shaft connected to the interior shaft over the bonded distal end of the balloon, the exterior shaft having a diameter greater than the exterior diameter of the stent.

A further aspect of the present invention provides for a stent made of interconnected elongate members of nonuniform cross-sectional area in order to minimize the amount of prosthetic material used and maximize the strength of the stent. In one embodiment, the cross section of the elongate members at a point between connecting nodes is less than that at a point adjacent to those nodes. In addition, a greater cross section may be provided at points adjacent to the nodes which are adjacent to the nodes at the axial ends (terminal nodes). In addition, the elongate members may have a rounded cross-sectional area to reduce the possibility of puncturing the expandable region of the catheter or damaging of the urethral lining.

In accordance with yet another embodiment of the stent, there is provided an elongate, cylindrical expandable stent, comprising a first end; a second end; a plurality of elongate members having a rounded, nonrectangular cross section extending from the first end to the second end; and a plurality of nodes interconnecting adjacent members, wherein the elongate members and the nodes are integrally formed from a single piece of material and the stent exhibits a generally smooth outer profile.

The present invention also includes a method for making a catheter having an expandable balloon positioned in a recess at the distal end thereof, comprising the steps of providing a catheter comprising an interior shaft having an outer diameter and a concentric exterior shaft having a second diameter that is greater than the outer diameter, wherein the exterior shaft terminates proximally of the distal end of the catheter and the interior shaft extends distally of the distal end of the exterior shaft; attaching an inflatable polymer balloon to the catheter so that the balloon is over the extending portion of the interior shaft and the distal end of the balloon is bonded to the interior shaft, and so that a distal-most portion of the interior shaft extends distally of the balloon; placing an expandable tubular stent over the balloon; and attaching an end piece over the distalmost portion of the interior shaft to retain the stent over the balloon, wherein the end piece has an outer diameter at least as great as the outer diameter of the stent. In a preferred embodiment, the outer diameter of the end piece is substantially the same as the diameter of the exterior shaft. In another preferred embodiment, the method further comprises the step of inflating the balloon to test the balloon prior to placing the stent over the balloon.

In accordance with still another aspect of the present invention, there is provided an apparatus for removing a previously positioned and expanded stent from a body channel, comprising an outer sheath having an inner lumen; a first attachment device within the lumen that is axially movable to extend axially out from the distal end of the lumen and extend radially grasp the end of an implanted, radially expanded stent; and a means for radially retracting and axially drawing the attachment device and an attached stent into the lumen, so that the axial movement of the attachment device pulling the stent into the lumen acts to radially compress the stent so that the stent can be drawn fully into the lumen. The attachment device preferably includes at least two or three radially projecting members for grasping a stent.

The present invention also includes a method for removing a previously positioned and expanded stent from a body passageway, comprising the steps of inserting a removal instrument having a proximal attachment means located in a lumen in a sheath into the passageway; extending the attachment means distally out of the sheath, radially extending the attachment means, and grasping the proximal end of the stent with the attachment means; radially retracting the attachment means and the grasped proximal end of the stent and drawing the attachment means and the stent into the distal end of the lumen so that the axial movement of the stent into the lumen serves to radially compress the stent and to draw the compressed stent into the sheath; and removing the instrument and the compressed stent from the passageway.

Further objects, features and advantages of the present invention will become apparent from the detailed description of preferred embodiments which follows, when considered together with the attached Figures.

BRIEF DESCRIPTION OF THE DRAWINGS

FIG. 1 is a perspective view of an apparatus according to the present invention, with the tubular stent in an unexpanded state.

FIG. 2 is a schematic detail view of the distal end of an apparatus according to the present invention, with the tubular stent in an expanded state.

FIG. 3 is a cross-sectional view taken along the line 3—3 in FIG. 2.

FIG. 4 is an enlarged, perspective view of the distal end of an apparatus in accordance with the present invention.

FIG. 5 is a perspective, sectional view of the distal end of an apparatus in accordance with the present invention.

FIG. 6 illustrates one embodiment of the side wall pattern of a tubular stent according to the present invention.

FIG. 7 is a cross-sectional view of a tubular stent of the present invention expanded to a configuration having a non-circular cross section.

FIG. 8 illustrates a modification of the side wall pattern illustrated in FIG. 6.

FIG. 9 is a perspective view of another embodiment of an expansion catheter according to the present invention.

FIG. 10 is a detailed perspective view of the distal end of the apparatus in FIG. 9.

FIG. 11 is an elevational, sectional view of the apparatus in FIG. 10.

FIG. 12 is a perspective view of a removal apparatus according to the present invention.

FIG. 13 is a sectional view of the removal apparatus of FIG. 12, engaging an expanded tubular stent.

FIG. 14 is a sectional view of the removal apparatus of FIG. 13, following axial elongation of the tubular stent.

FIG. 15 is a simplified schematic view of the apparatus of the present invention shown in FIG. 1, with a generally convex balloon and corresponding tubular stent illustrated in the expanded state.

DETAILED DESCRIPTION OF PREFERRED EMBODIMENTS

Figure 16:
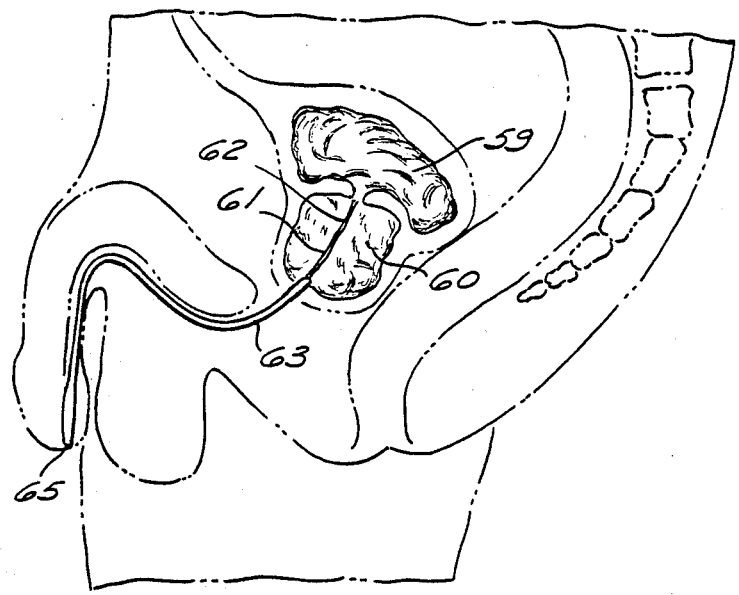
FIG. 16 is a simplified sectional view of the region of the male pelvis showing the urethra, prostate gland and bladder.

Expansion Catheter of FIGS. 1-5 and 20

Referring to FIGS. 1-5 there is illustrated an expansion catheter according to the present invention, which is this embodiment comprises a balloon catheter, having an axially elongate, catheter shaft 2. The proximal, control end of the catheter 1 may be equipped as would be the control end of known angioplasty balloon catheters such as that disclosed in U.S. Pat. No. 4,573,470 to Samson, et al. The embodiment of the present invention illustrated in FIG. 1 has an inflation port 3 and optimally a distinct vent port 4, each in fluid communication, respectively, with an inflation lumen 5 and vent lumen 6 (illustrated in FIG. 3) extending axially through the catheter. Inflation lumen 5 is in fluid communication at the distal end thereof with the interior 7 of an expandable balloon 8 by means of at least one inflation duct 9 through the wall 10 of the catheter proximal lumen 5 and adjacent the interior surface of balloon 8. Similarly, vent lumen 6 is in fluid communication with the interior 7 of balloon 8 by means of at least one vent duct 11, proximal to inflation duct 9. At the commencement of filling the balloon, any air in the lumen 5, 6 or in the interior 7 of balloon 8 will be chased out of vent port 4, which may then be sealed by a stopcock or other means (not illustrated).

A third lumen 12 may be provided for receiving a radiopaque dye introduced by way of dye port 14 at the proximal end thereof. A guidewire 13 may also be inserted through dye port 14 and lumen 12.

Near the distal, functional end of the catheter, a region 10 of the catheter shaft 2 is reduced in diameter to provide an annular depression 15 defined axially by a proximal annular shoulder 16 and a distal annular shoulder 17 on catheter shaft 2. The axial length of the annular depression preferably corresponds to the desired length of a stent 18 to be inserted in a given application. Referring to FIG. 3, there is disposed concentrically about the reduced catheter wall 10 and at the radially inward most region of the annular depression 15, annular inflatable balloon 8 in fluid communication with said inflation lumen 5 by way of duct 9. An expandable, tubular stent 18 having a central lumen 19 therethrough (illustrated in FIG. 7), discussed infra, is coaxially disposed about the balloon 8.

The expansion catheter 1 of the present invention is designed so that the outer, substantially cylindrical profile of the catheter is uninterrupted by the presence of the expandable stent 18, in its unexpanded state. Accordingly, in the case of a balloon catheter, the outer diameter of the collapsed balloon 8 is smaller than the outer diameter of shoulders 16, 17 of the adjacent catheter shaft 2, so that the collapsed balloon 8 only partially fills the annular depression 15 formed between the annular shoulders 16 and 17, in the radial direction. The unexpanded stent 18 is disposed coaxially about balloon 8 and between shoulders 16 and 17 such that the stent 18 and adjacent catheter shaft 2 comprise a substantially cylindrical configuration. This configuration enables insertion of the apparatus without the need for a sheath.

The material of the balloon 8 is in the form of a tubular sleeve which extends the length of the catheter 1 and is adhered to the wall of the catheter shaft 2 proximal to shoulder 16 and distal to shoulder 17 but not in the region 15 where it forms balloon 8 and is permitted to expand.

Introduction of pressurized fluid into the interior 7 of balloon 8 by way of inflation lumen 5 causes radial expansion of the balloon 8, which in turn causes a radial expansion of the stent 18 disposed concentrically therearound. Once expanded by inflating the balloon 8, the inner diameter of the central lumen 19 through expanded stent 18 is greater than the outer diameter of the catheter shaft 2 in the region between the annular depression 15 and the distal end of the catheter 1, including shoulder 17. Thus, following deflation of the balloon 8, the catheter 1 may be withdrawn through the central lumen 19 of stent 18 leaving the expanded stent 18 in place within the prostatic urethra, as will be detailed infra in connection with the method of the present invention.

The outer diameter of the catheter is preferably minimized, to facilitate insertion and to avoid side effects and complications resulting from stretching of the urethra. There may be provided in accordance with the present invention a graduated set of graft-catheter systems with different sizes to suit individual patient requirements.

The catheter may be provided with a flexible, resilient catheter tip 20 at the distal end thereof. The tip 20 is preferably formed with a tapered or rounded configuration to minimize damage to the urethral lining and further to ease in insertion of the catheter into the collapsed lumen of the urethra.

Figure 20:
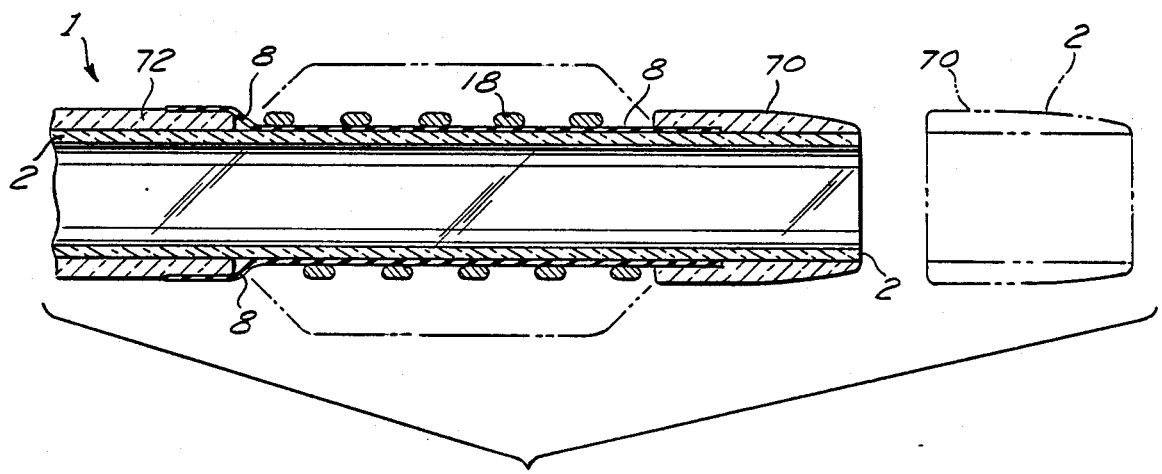
FIG. 20 is a sectional view of the distal end of a catheter with a stent and end piece.

Referring to FIG. 20, the catheter tip 20 is comprised of an end piece 70 which has an outer diameter at least as great as the outer diameter of the stent 18, and preferably has a diameter that is the same as or greater than the exterior shaft 72. It is preferable that the end piece 70 has an outer diameter substantially the same as the outer diameter of the exterior shaft. As in the catheter tip 20, the end piece 70 may advantageously be made of flexible, resilient material and is preferably formed with a tapered or rounded configuration. The end piece 70 is removably attached to the distal end of the catheter 1 and preferably terminates distally with interior shaft 2. As indicated in FIG. 20, the end piece 70 may be attached about balloon 8. End piece 70 acts to securely fasten stent 18 about balloon 8.

Because end piece 70 is not integrally a part of interior shaft 2, but is attached thereto during the construction process, the invention provides for an improved method of constructing catheter 1. One places an exterior shaft 72 over the interior shaft 2, the exterior shaft 72 having an interior diameter about the same as the outer diameter of the interior shaft 2. The exterior shaft 72 is formed to terminate proximally of the distal end of catheter 1, so that interior shaft 2 extends distally of the exterior shaft 72. Then balloon 8 is attached to catheter so that it covers the distal-most portion of exterior shaft 72, or is at least adjacent to or abuts against and also covers a portion of the interior shaft 2 which extends distally beyond exterior shaft 72. The distal end of the balloon 8 is bonded to the interior shaft 2. Next, one places stent 18 over the balloon 8, and finally attaches the end piece 70 to prevent the stent 18 from sliding distally. The distal end of the exterior shaft 72 similarly prevents the stent 18 from sliding proximally.

The improved method also preferably comprises testing the balloon 8 prior to placing the stent 18 over the balloon 8. Once it is determined that the balloon 8 is capable of withstanding a predetermined internal pressure, it is deflated and then the stent 18 is positioned about the balloon 8. Finally, the end piece 72 is secured over the extending portion of the interior shaft 2 and preferably also over the distal-most portion of the balloon 8.

Expansion Catheter of FIGS. 9-11

Another embodiment of an expansion catheter according to the present invention is illustrated in FIGS. 9-11. In this embodiment, there is provided an elongate catheter shaft 2 having an elastic sheath 21 disposed therearound. The shaft comprises an elongate sleeve 22 having a female thread 23 on the interior thereof. Rotatably positioned within the sleeve 22 is an elongate shaft 24 having a male thread 25 for engaging the female thread 23 on sleeve 22. The threaded region, illustrated in FIG. 11 near the distal ends of shaft 24 and sleeve 22, extends in an axial direction for a sufficient distance to permit the expansion member 32 to be fully drawn into the conical space 34 as will become apparent. In the illustrated embodiment, a first knob 26 is rigidly secured to the proximal end of shaft 24, and a second knob 27 is secured to the proximal end of sleeve 22.

A plurality of axially oriented floating segments or tines 28 are movably disposed distal to the end of sleeve 22. The exterior surfaces 29 of the tines 28 are held in place by the elastic sheath 21 and cooperate to form a generally cylindrical exterior profile, for receiving an unexpanded tubular stent 18. The radial thickness of the tines 28 tapers from the thickest dimension near the proximal end 30 of tine 28 to the thinnest dimension near the distal end 31 of tine 28, thereby defining a roughly cone-shaped interior space 34.

A cone-shaped expansion member 32 is attached at its pointed end to elongate shaft 24. Rotation of knob 26 in a first direction relative to knob 27 draws elongate shaft 24 axially in a proximal direction, moving expansion member 32 into the cone-shaped space 34 formed by the tines 28. Further rotation of knob 26 in a first direction relative to knob 27 results in expansion member 32 effecting a radial outward expansion of tines 28, which in turn causes a radial outward expansion of the expandable stent 18. Rotating the knob 26 in the reverse relative direction causes expansion member 32 to back out of space 34. The resilient nature of the elastic sheath 21 causes tines 28 to return back to their unexpanded configuration, when permitted by movement of member 32 in a distal direction. The tubular elastic sheath 21 extends beyond the end of expansion member 32 at which point it merges with an integrally formed blunt end 33. As illustrated in FIG. 11, the outer diameter of blunt end 33 and of the sheath 21 proximal to stent 18 are slightly enlarged so that the exterior configuration of the expansion catheter, with the stent mounted thereon is substantially uniform and generally smooth along its axial length.

Stent Removal Apparatus

Another aspect of the present invention provides an apparatus for removing a previously positioned and expanded stent, under direct endoscopic vision. Referring to FIGS. 12-14, the apparatus comprises a catheter shaft 35, having proximal and distal attachment means 36 and 37 attached thereto and adapted to engage the corresponding proximal and distal ends 38 and 39 of the implanted stent. The attachment means are capable of movement, relative to each other, along the axial direction of the removal instrument.

In the illustrated embodiment, the proximal attachment means 36 comprises a plurality of tines 40, inclined in the proximal direction and mounted to a sleeve 41 which extends the length of the catheter shaft 35. A first knob 42 is secured to the proximal end of sleeve 41, in proximity with a second knob 43 attached to the proximal end of an elongate shaft 44 which extends through sleeve 41. The interior surface of sleeve 41 may be provided with a female thread for engaging a male thread on the shaft 44, in the manner illustrated in FIG. 11, illustrating an expansion catheter of the present invention. The important relationships that the shaft 44 is capable of reciprocating movement within the sleeve 41, as will become apparent.

The distal attachment means 37 comprises a ring 45 which is rotatably attached near the distal end of shaft 44 by engaging an annular groove on said shaft 44 or other conventional means. A plurality of tines 46 are attached to the ring 45, said tines 46 radiating outward and inclined in a distal direction.

An outer sheath 47 is slidably mounted on the outside of sleeve 41. The interior lumen of sheath 47 is flared at the distal end 48 thereof so that the sheath 47 may be slid down over tines 40, causing them to resiliently bend radially inwardly yet remain inclined in the proximal direction. To help ensure that the tines 40 are not bent towards the distal direction by the sheath 47, the outer surface of tines 40 may be provided with a rounded edge 49. The mechanical features of the removal instrument will be made more clear by reference to the discussion of the method of removing an implanted stent, infra.

Expandable Tubular Stent

Referring to FIG. 4, there is illustrated a radially expandable tubular stent 18 according to the present invention, the stent being illustrated in its unexpanded, substantially cylindrical configuration and mounted on a balloon catheter. The wall thickness of the stent is advantageously from about 0.0003 to about 0.06 inches, preferably is from about 0.005 to about 0.025 inches, and more preferably is from about 0.008 to about 0.012 inches. The wall of the stent is formed with a plurality of passages therethrough, as best illustrated in FIGS. 6, and 8, which depict wall patterns as they might appear if the wall of the stent 18 were rolled out flat. In FIG. 6, a first plurality of parallel filaments 50 are aligned at a diagonal to a second plurality of parallel filaments 51, all formed from a single piece of material to yield a diamond pattern having a plurality of diamond shaped openings 52 therethrough. This configuration of the filaments 50 and 51 permits radial outward deformation of the tubular stent 18 in response to a radial outward force exerted by the expansion catheter 1 of the present invention. Construction of the stent from a malleable, biologically compatible metal such as titanium, or other materials discussed infra permits the stent 18 to hold its expanded configuration under stress exerted by, for example, a hypertrophied prostate gland, thereby maintaining patency in an otherwise stenotic or occluded lumen. In addition, orientation of filaments 50 and 51 is such that forces exerted upon the axial ends 38, 39 of an expanded tubular stent 18 in opposite axial directions will effect an axial elongation of the stent 18 and a consequent reduction in the diameter thereof.

A variation of the wall pattern of FIG. 6 is illustrated in FIG. 8, wherein the roughly diamond shaped openings become smaller near the axial ends of the stent 18. This configuration facilitates greater expansion in the central region 64 thereof, and, like the pattern in FIG. 6, permits the expanded stent 18 to be reduced in diameter by applying an axially elongating force thereto.

The ratio of solid wall area to the total area of the opening therethrough is relatively low. This minimizes contact area between the material of the stent and the lining of the lumen, may improve the expansion characteristics of the stent, and minimizes interference with vessels entering the urethral lumen from the side, such as the prostatic ducts, and the terminal portion of the ductus deferens, which transverses the prostate to empty into the urethra. In addition, the transverse openings through the wall of the stent may promote tissue ingrowth thereby minimizing encrustation of the filament portions 50 and 51, of the stent by dissolved minerals, reducing the risk of migration of the stent in the direction of the bladder.

Optimally, the wall thickness of any given stent will be substantially uniform throughout, however, in one embodiment of the present invention, the wall is thinner in the central region 64. The thickness of the stent wall as measured in the radial direction may be different in different stents in order to permit a greater or lesser area of transverse openings therethrough, while maintaining structural integrity of the stent. It is important that the stent 18 be capable of withstanding the constant radially inward directed force exerted by a hypertrophied prostate gland.

The axial length of the stent 18 should be sufficient that pressure exerted by the hypertrophied prostate cannot cause stenosis of the lumen beyond the axial ends thereof. The length of the stent will often be from about 1 cm to about 4 cm, dependinq upon the location and extent of the hypertrophy or hyperplasia, is preferably from about 1.5 to about 3.0 cm in length and most preferably is about 2.4 cm in length, which is the average approximate length of the prostatic urethra.

Preferably the stent of the present invention will be made using a biocompatible material, either throughout, or in the form of a coating over the stent, which will improve its compatibility with the physiological and chemical environment within the urethral lumen. For example, the stent will be exposed to urine having a pH in the range of from about 4.5 to 8, a relatively wide variation compared to other body fluids such as blood, which generally has a pH of about 7.4. The coating may be a plastic or polymeric material, such as a fluoropolymer, for example polytetrafluoroethylene, or preferably silicone rubber. Alternatively, the coating may be isotropic carbon, and the surface of the stent may be either smooth or microporous in nature. It is believed that a smooth surface is desirable because irregularities in the surface may provide sites for precipitation of salts due to the relatively high osmolality of urine. A sufficiently smooth surface would thus minimize encrustation of the stent. A surfactant or chelating agent may advantageously be affixed to the surface of the stent, for further reducing encrustation thereof.

The maximum expanded diameter of the stent 18 will likely be within the range of from about 10 mm to about 14 mm or greater. This range refers to the largest cross-sectional dimension in the case of stents which are enlarged to a configuration having a non-circular cross section or a non-cylindrical profile. Depending upon its construction material and physical design, a given stent may be expanded within an optimal range, which may be less than the overall ranges indicated above.

Figure 18:
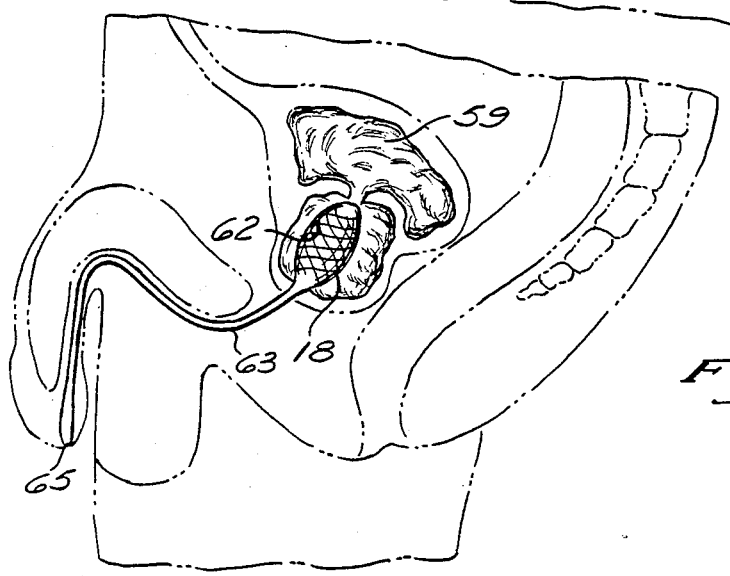
FIG. 18 is the sectional view of FIG. 16, illustrating another embodiment of the expanded stent of the present invention within the prostatic urethra.

The stent 18 of the present invention may be expanded from a first, unexpanded configuration to a second, expanded state having a substantially uniform cross section throughout the axial length thereof, or to a configuration having a greater cross-sectional area in the central region than in the regions near the axial ends thereof. This latter configuration is achieved, for example, by a mechanical design of the stent 18 which permits greater expansion in the central region, such as by slotting with greater frequency in the case of a malleable metal stent, or by choice of a material for the central region of the stent having greater expansion abilities than a different material incorporated into the axial end regions 38 and 39. For example, the sidewall pattern illustrated in FIG. 8 would permit greater radial expansion near the center than at the axial ends. Alternatively, graduated wall thicknesses on a stent of uniform composition could be employed. Preferably, however, the configuration of the expanded stent 18 corresponds to the expanded shape of the balloon 8 used to accomplish its expansion. Thus, the catheter 1 of the present invention may be provided with balloons 8 having a variety of fully inflated profiles, for example, cylindrical, concave, convex or frusto-conical, to suit any of a variety of clinical indications. FIGS. 15 and 18, for example, illustrates a stent that has been expanded by a balloon having a convex profile.

In the embodiment illustrated in FIGS. 15 and 18, migration of the stent 18 is minimized due to the restrictive forces caused by the normal tissue in the area of the bladder neck. The enlarged midsection 64 of the stent 18 would be unable to pass through the restricted neck of the bladder because any forces tending to cause migration would generally be insufficient to force a stent of this configuration axially through the urethra. For similar reasons, migration of the stent away from the bladder would also be minimized.

In addition, the stent is advantageously expanded to have an oval or otherwise non-circular cross-sectional area, such that as illustrated in FIG. 7. The stent is advantageously expanded to have a configuration which closely approximates the cross-sectional shape of the native prostatic urethra, and may permit normal contractions of the prostate gland.

According to another embodiment of the stent 18 of the present invention, the axial end regions 38, 39 of the stent 18 are softer or more flexible than the region in the center of the stent 18 thereby allowing a smooth transition from the lumen 19 of the stent 18 to the lumen of the urethra. The axial end regions 38, 39 of the stent may be formed with a gradual taper in a radial inward direction, thereby reducing the risk of stress and irritation, and possibly even kinking of the urethral lining at the grafturethra lumen juncture.

Referring to FIG. 16, there is illustrated in simplified form a sectional view of the male pelvic region, showing the bladder 59, an enlarged or hypertrophied prostate gland 60 causing a stenosis 61 of the prostatic urethra 62. Thus, the interior diameter of the prostatic urethra 62 has become smaller than the interior diameter of the non-prostatic urethra 63.

Figure 17:
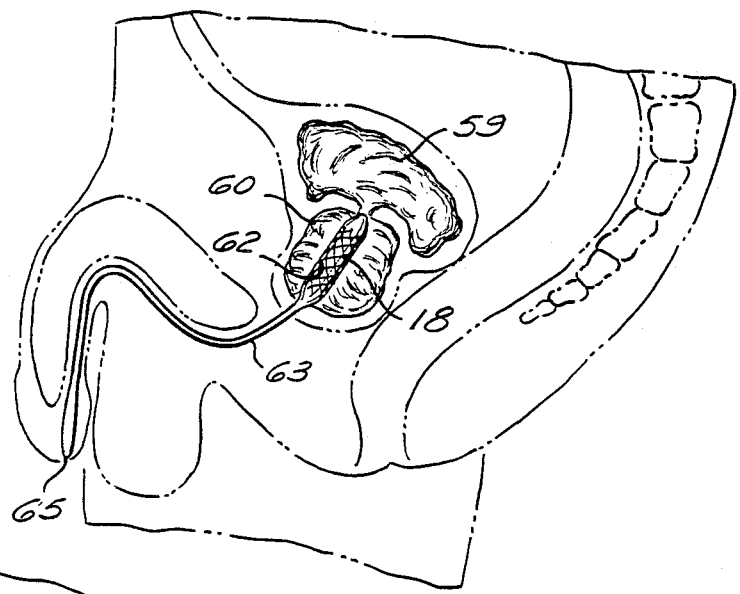
FIG. 17 is the sectional view of FIG. 16, illustrating an expanded stent of the present invention within the prostatic urethra.

Referring next to FIG. 17, there is illustrated an expanded stent 18 within the prostatic urethra 62, having a substantially uniform cross section throughout the midsection 64 thereof, and a radially inwardly directed taper near the axial ends 38 and 39. The expanded state diameter of the stent 18 is slightly exaggerated for illustration. Referring to FIG. 18, there is illustrated an expanded stent 18 in position within the prostatic urethra 62, having a generally convex exterior configuration throughout its axial length. In this latter preferred inflated state configuration, the resilient force exerted by the prostate gland 60 acts in cooperation with the generally convex stent 18 to minimize the likelihood of migration of stent 18 into the interior of bladder 59, or into the urethra 63 downstream of the prostatic urethra 62.

A malleable metal stent according to the present invention, comprising, for example, titanium, may be manufactured by first machining titanium tube or sheet stock to the desired wall thickness, generally in the range of from about 0.004 to about 0.05 inches, and then cutting or etching the wall pattern thereon, such as one of those patterns illustrated in FIGS. 6 or 8. The cutting may advantageously be accomplished using conventional electron discharge machining equipment. Tube stock may be cut on a revolving mandrel, whereas sheet stock may be cut in sheet form and subsequently rolled into tubular form, welded and polished.

Figure 19:
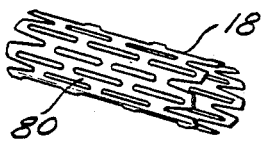
FIG. 19 is a perspective view of a tubular stent in an unexpanded state.
Figure 21:
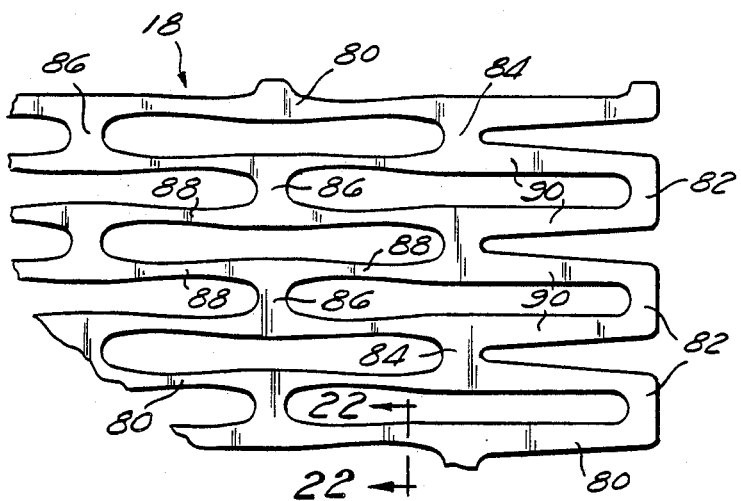
FIG. 21 is a flattened projection of a portion of the wall of a stent.

FIGS. 19–23 disclose a preferred embodiment of the expandable tubular stent 18. In FIGS. 19 and 21, filaments 50 and 51 are now of substantially parallel elongate members 80 and connecting nodes 82, 84, and 86. As more clearly shown in FIG. 21, nodes 82 are located at the axial ends of stent 18 and are referred to herein as terminal nodes. Nodes 84 are those which are immediately adjacent to terminal nodes 82 and are referred to herein as secondary nodes. All other nodes not either terminal or secondary nodes are referred to herein as interior nodes 86.

In a preferred embodiment, interior nodes 86 are arranged along the length of elongate members 80 so that, progressing from one end of stent 18 to the other along its concentric axis, elongate member 80 is connected alternately to other elongate members 80 on either side of it. To maximize the strength of stent 18 and simultaneously minimize the amount of prosthetic material used in constructing stent 18, elongate members 80 have nonuniform cross sections. For example, because bending forces are less at points 88 midway between interior nodes 86, it is preferred that a smaller cross-sectional area be found at point 88 (midway between nodes) as compared to a point adjacent to interior node 86. However, the elongate member 80 may not become so thin at point 88 so as to bend there instead of at points adjacent to the interior node 86. Similarly, a greater cross-sectional area of elongate member 80 preferably should be used at point 90 adjacent to secondary node 84 on the terminal side because it is here that greater bending forces are experienced. It is preferable that the material at point 90 be of sufficient thickness and cross-sectional area amount that elongate member 80 between terminal node 82 and secondary node 84 is capable of withstanding radial compression to an increased degree, preferably to substantially the same degree as elongate member 80 at points between interior nodes 86. The non-uniform thicknesses of elongate members 80 has been exaggerated in FIG. 21 for illustration.

Figure 22:
FIG. 22 is a sectional view taken along the line 22—22 in FIG. 21.
Figure 23:
FIG. 23 is another sectional view taken along the line 22—22 in FIG. 22.

FIGS. 22 and 23 show two preferred cross sections of elongate member 80. In preferred embodiments, elongate member 80 has a rounded non-rectangular cross section so that the possibility of damaging the urethral lining or puncturing the balloon 8 is minimized.

The cross section shown in FIG. 23 is rounded primarily on its exterior surface, so that it assumes a "D"-shaped configuration. The cross section shown in FIG. 22, on the other hand, is rounded on both its interior and exterior edges, so that it assumes an oval or circular cross section.

The edges of the elongate members of the stent 18 may be rounded by any appropriate means. However, it is believed that extrusion honing, where an abrasive slurry is directed against the edge to be rounded, is a particularly appropriate technique.

Method of Placement and Dilation of Expandable Tubular Stent

In accordance with the insertion method of the present invention, a dilation means 1 having a suitable expandable stent 18 associated therewith is selected and then transurethrally positioned within the prostatic urethra 62 by way of the external opening 65 of the urethra 63. The positioning step may advantageously be accompanied by or preceded by the introduction of a radiopaque dye through dye port 14, from which it will be conducted via lumen 12 through the catheter 1 to the area of stenosis 61, to enable visualization thereof. The positioning step may also advantageously be preceded by coating the catheter 1 and stent 18 disposed thereon with a water soluble surgical jelly or other lubricant, such as Surgilube ®, a sterile, bacteric-static surgical lubricant, available from E. Fougera & Co., Melville, N.Y. Positioning may also be accomplished with the use of a guidewire 13, in accordance with known catheterization techniques.

With the balloon catheter 1 in position, a pressurized fluid is introduced into inflation port 3 which, by way of lumen 5 and inflation duct 9 enters the balloon 8. Vent port 4 may be vented until all air has been purged, at which time it is sealed by closing a stopcock or other conventional means. Inflation of the balloon 8 causes radial expansion of the expandable stent 18 and also dilation of the surrounding lumen against the pressure exerted by the hypertrophied prostate gland 60. The radially expandable stent 18 is advantageously dilated sufficiently that the inside diameter of the lumen 19 therethrough exceeds the outer diameter of the region of the catheter between the annular depression 15 adapted to receive the undilated stent 18 and the distal tip 20 of the catheter 1, so that the catheter 1 may be withdrawn through the lumen 19 of the expanded stent 18 leaving said stent 18 in place within the prostatic urethra.

By varying the configuration of the balloon 8 in the case of a balloon catheter, as previously discussed, the stent 18 may be expanded to a final shape having a substantially circular cross section, or a cross section that more closely adheres to the natural configuration of the normal lumen inside the urethra.

Following dilation of the intraluminal stent 18, the dilating catheter 1 may be reduced in diameter by exhausting the pressurizing fluid under any contractile force of the balloon 8 and then evacuating the contents of the balloon 8 by way of inflation port 3. The apparatus may then be withdrawn through the lumen 19 of stent 18, leaving the expanded stent 18 in place within the prostatic urethra 62, illustrated in FIGS. 17 and 18.

Method for Subsequent Dilation of Expandable Tubular Stent

The apparatus 1 may at a later time be reinserted, via the external opening 65 of the urethra 63, should it become necessary to further increase the diameter of the stent 18 within urethral lumen 62 or to redilate the expandable stent 18. According to this aspect of the process of the present invention, a previously positioned and dilated stent 18 is fluoroscopically visualized in accordance with known techniques. An appropriate catheter having a balloon 8 with the desired inflated state configuration is selected, transurethrally inserted as discussed supra, and positioned with the deflated balloon 8 coaxially disposed within the prepositioned, expanded stent 18. For this purpose, the catheter 1 may be provided with one or more radiopaque markers 66 for visualization of the location of the balloon 8. The balloon 8 is then inflated, re-expanding, further expanding, or altering the configuration of the stent 18. Thereafter, the balloon 8 may be deflated, and the catheter 1 is withdrawn, leaving the re-expanded stent 18 within the prostatic urethra 62.

Method for Removal of Expanded Tubular Stent

In yet a further aspect of the process of the present invention, a prepositioned stent 18 may be removed through the use of a removal instrument equipped such as that illustrated in FIG. 12 with attachment means 36 and 37, described supra, and adapted for insertion through the operating channel of a urethroscope or cystoscope. The urethroscope is transurethrally inserted, by way of the external opening 65 of the urethra 63, and positioned such that the previously positioned stent 18 may be directly visually observed. Under direct observation, the removal instrument is positioned coaxially within the prepositioned stent 18 by way of the operating channel of the urethroscope. During this positioning step, the sheath 47 is slid axially in a distal direction to cover distal attachment means 37. When both attachment means 36 and 37 are positioned within the lumen 19 of an expanded stent 18, the sheath 47 is axially retracted, exposing said attachment means 36 and 37. The tines 40 and 46 resiliently bend in a radial outward direction in the absence of sheath 47, until they reach approximately a diagonal as illustrated in FIG. 13. As shaft 44 is axially extended, e.g., by rotating knob 43 while knob 42 is held stationary, the proximal tines 40 will engage the proximal end 38 of the stent 18 by extending through the openings 52 or 58 illustrated in FIGS. 6 and 7. In a similar manner, the distal attachment means 37 is caused to engage the distal end 39 of the stent 18. The attachment means are thereafter moved further apart in an axial direction, causing an axial elongation of the implanted stent 18. Due to the configuration of the side wall of the stent 18, a reduction in the radius of the stent 18 results. Once sufficiently reduced in diameter, the sheath 47 is slid distally to cover both attachment means 36 and 37, having the radially reduced stent 18 attached therebetween. The urethroscope and the removal instrument, having the elongated stent 18 still engaged, may thereafter be transurethrally withdrawn.

Alternatively, the stent removal apparatus may include only a portion of the structure illustrated in FIGS. 12–14. Specifically, the apparatus may have only a proximal attachment means 36, which can be any suitable structure for grasping the proximal end of an expanded stent 18 which has been implanted by radial deformation thereof. The tines, projections, grasping members, or other suitable attachment structure of the proximal attachment means is adapted to extend out from the outer sheath 47, expand out to grasp the proximal end of the stent 18, contract radially and withdraw back into the outer sheath, and draw the stent 18 into the interior lumen of the distal end 48 of the sheath 47. Because the lumen is of a smaller diameter than the expanded stent (except for the contracted proximal end of the stent 18, which has already been drawn into the lumen), axial force exerted on the proximal end of the stent 18 forces the indrawn stent 18 to lengthen, and forces the expanded portion of the stent 18 to radially contract as it is drawn inside the sheath 47.

Although this invention has been described in terms of certain preferred embodiments, other embodiments that are apparent to those of ordinary skill in the art are also within the scope of the invention. Accordingly, the scope of the invention is intended to be defined only by reference to the appended claims.

What is claimed is:

1. An apparatus for relieving the symptoms of hypertrophy of the prostate gland, comprising:
    an axially elongate catheter shaft comprising at least one lumen therethrough and having an annular recess thereon for receiving a stent;
    an expandable balloon mounted on said shaft in said recess and in communication with said lumen; and
    a removably mounted, radially outwardly deformable and expandable tubular stent coaxially disposed about said balloon and situated in said recess, wherein said stent has an opening at each axial end and a central lumen therethrough, wherein said stent is radially expandable by deformation to a preselected configuration in response to pressure from said balloon, and the outside diameter of the stent, in its unexpanded state, is not substantially greater than the outside diameter of the adjacent catheter shaft, and wherein said adjacent catheter shaft has a substantially uniform diameter.

2. An apparatus as in claim 1, wherein said balloon in its expanded state has a non-cylindrical configuration.

3. An apparatus as in claim 1, wherein said balloon in its expanded state has a smaller cross-sectional area at its axial ends than in the central region thereof.

4. An apparatus as in claim 1, wherein said catheter further comprises a lumen for receiving a guidewire therethrough.

5. An apparatus as in claim 1, further comprising at least one radiopaque marker associated with the axial position of said balloon.

6. An apparatus as in claim 1, wherein said balloon expands to a configuration having a non-circular cross section, and a convex profile along its axial length.

7. An apparatus as in claim 1, further comprising a biocompatible, essentially smooth coating on said stent.

8. An apparatus of claim 1, wherein the catheter shaft distal of said recess comprises:
    an interior shaft having a diameter no greater than the interior diameter of said stent, wherein the distal end of said balloon is bonded to said interior shaft; and
    an exterior shaft connected to said interior shaft over said bonded distal end of said balloon, said exterior shaft having a diameter at least as great as the exterior diameter of said stent.

9. An elongate, cylindrical expandable stent, comprising:
    a first end;
    a second end;
    a plurality of elongate members extending from said first end to said second end;
    a plurality of nodes interconnecting adjacent members, said nodes arranged along the length of said adjacent members so that, progressing from said first end to said second end, each member is alternately connected to members on either side thereof, and wherein the cross-sectional area of each said member is non-uniform, such that for at least one node along the length of each member, the cross-sectional area of said member is greater adjacent to said one node than at a point removed from said one node.

10. An elongate, cylindrical expandable stent, comprising:
    a first end;
    a second end;
    a plurality of elongate members having a rounded, non-rectangular cross section extending from said first end to said second end; and
    a plurality of nodes interconnecting adjacent members, wherein said elongate members and said nodes are integrally formed from a single piece of material and said stent exhibits a generally smooth outer profile.

11. The stent of claim 9 or 10, wherein said members are generally parallel to each other.

12. The stent of claim 9 or 10, wherein each member is connected to adjacent members at at least four nodes arranged along the length of each member, and wherein said nodes comprise terminal nodes located at said first end and at said second end, secondary nodes adjacent to said terminal nodes, and interior nodes between said secondary nodes, wherein the cross sectional area of said members where they connect to said secondary nodes is greater on the terminal side of said secondary nodes than on the interior side of said secondary nodes.

13. The stent of claim 9, wherein the said members are nonrectangular and rounded in cross section.

14. A method for making a catheter having an expandable balloon positioned in a recess at the distal end thereof, comprising the steps of:
    providing a catheter comprising an interior shaft and a concentric exterior shaft over said interior shaft, said exterior shaft having an outer diameter that is greater than the outer diameter of said interior shaft, wherein said exterior shaft terminates proximally of the distal end of said catheter and the interior shaft extends distally of the distal end of said exterior shaft;
    attaching an inflatable balloon to said catheter so that the balloon is over the extending portion of said interior shaft, the proximal end of the balloon is bonded over the distal end of the exterior shaft, and the distal end of said balloon is bonded to said interior shaft, and so that a distal-most portion of said interior shaft extends distally of said balloon;

placing an expandable tubular stent over said balloon; and attaching an end piece over said distal-most portion of said interior shaft to retain said stent over balloon, wherein said end piece has an outer diameter at least as great as the outer diameter of said stent.

15. The method of claim 14, wherein the outer diameter of said end piece is substantially the same as the diameter of said exterior shaft.

16. The method of claim 15, further comprising the step of inflating said balloon to test said balloon prior to placing said stent over said balloon.

17. The apparatus of claim 1, wherein said stent is as defined in any one of claims 9 to 13.

* * * * *

UNITED STATES PATENT AND TRADEMARK OFFICE
CERTIFICATE OF CORRECTION

PATENT NO. : 4,893,623

DATED : January 16, 1990

INVENTOR(S) : Robert F. Rosenbluth

It is certified that error appears in the above-identified patent and that said Letters Patent is hereby corrected as shown below:

```
Column 6, line 16, change "catheter according" to
--catheter 1 according--

Column 7, line 64, change "catheter so" to
--catheter 1 so--

Column 14, line 18, change "catheter having" to
--catheter 1 having--
```

Signed and Sealed this

Second Day of June, 1992

Attest:

DOUGLAS B. COMER

*Attesting Officer*   *Acting Commissioner of Patents and Trademarks*